US006455077B2

(12) United States Patent
Katiyar et al.

(10) Patent No.: US 6,455,077 B2
(45) Date of Patent: Sep. 24, 2002

(54) HERBAL COMPOSITION AND METHOD OF MANUFACTURING SUCH COMPOSITION FOR THE MANAGEMENT OF GYNECOLOGICAL DISORDERS

(75) Inventors: Chandra Kant Katiyar; Ramesh Kumar Duggal; Bodapati Venkata Jagannadha Rao, all of Delhi (IN)

(73) Assignee: Dabur Research Foundation (IN)

( * ) Notice: Subject to any disclaimer, the term of this patent is extended or adjusted under 35 U.S.C. 154(b) by 0 days.

(21) Appl. No.: 09/819,828

(22) Filed: Mar. 28, 2001

(51) Int. Cl.$^7$ ............................................... A61K 35/78
(52) U.S. Cl. ...................... 424/725; 424/732; 424/734; 424/756; 424/757; 424/725
(58) Field of Search ................................ 424/725, 732, 424/734, 756, 757, 733

(56) References Cited

U.S. PATENT DOCUMENTS

| | | | | |
|---|---|---|---|---|
| 4,923,697 | A | * | 5/1990 | Albeck et al. |
| 5,552,416 | A | | 9/1996 | Keohane |
| 5,693,327 | A | * | 12/1997 | Shah |
| 6,080,401 | A | * | 6/2000 | Reddy et al. |
| 6,124,268 | A | * | 9/2000 | Ghosal |

FOREIGN PATENT DOCUMENTS

| | | | | |
|---|---|---|---|---|
| CN | 1107735 | A | * | 9/1995 |
| JP | 61115029 | A | * | 6/1986 |
| JP | 62067027 | A | * | 3/1987 |
| JP | 62099331 | A | * | 5/1987 |
| JP | 04069343 | A | * | 3/1992 |
| JP | 07118135 | A | * | 5/1995 |
| JP | 07147903 | A | * | 6/1995 |
| JP | 07157420 | A | * | 6/1995 |
| JP | 08012586 | A | * | 1/1996 |
| JP | 10226787 | A | * | 8/1998 |
| SU | 920395 | B | * | 8/1982 |

OTHER PUBLICATIONS

PDR for Herbal Medicines, Medical Economics Company, 1988, p. 638, 1071–1072, 1155–1156.*
Galle, P.C. et al., "Abnormal Uterine Bleeding," *Postgraduate Medicine*, vol. 93, No. 2, Feb. 1, 1993.
Bayer, Steven R. et al., Clinical Manifestations and Treatment of Dysfunctional Uterine Bleeding, *JAMA*, vol. 269, No. 14, Apr. 14, 1993.
Howkins and Bourne, *Shaw's Textbook of Gynaecology*, 10$^{th}$ edition, B. I. Churchill Livingstone Pvt Ltd., New Delhi, pp. 318–321.
Miksicek, R. J., "Commonly Occurring Plant Flavonoids have Estrogenic Activity," *Molecular Pharmacology*, 44:37–43, 1993.
Satyavati, G.V. et al., "Further Studies on the Uterine Activity of Saraca Indian Linn," *Indian J Med Res 58*, Jul. 7, 1970.
Sharma P. V., *Classical Uses of Medicinal Plants*, ed. Chaukhambha Visvabharati, pp. 26–27.
Sharma P. V., *Classical Uses of Medicinal Plants*, ed. Chaukhambha Visvabharati, pp. 331–333.
Sharma P. V., *Classical Uses of Medicinal Plants*, ed. Chaukhambha Visvabharati, pp. 39–41.
*The Wealth of India*, Raw Materials vol. X: Sp–W, ed. Publications & Information Directorate, CSIR, New Delhi, pp. 90–91.
*The Wealth of India*, Raw Materials vol. X: Sp–W, ed. Publications & Information Directorate, CSIR, New Delhi, pp. 86–87.
Bhaishajyaratnavali, Ashokarishta.
Chunekar, K.C., et al. Bhav Prakhash Nighantu, 23. Ashoka (Ral Ashoka).
Chunekar, K.C., et al. Bhav Prakhash Nighantu, 63. Dhataki.
Chunekar, K.C., et al. Bhav Prakhash Nighantu, 75. Lodhra.

* cited by examiner

Primary Examiner—Leon B. Lankford, Jr.
Assistant Examiner—Ruth A. Davis
(74) Attorney, Agent, or Firm—King & Spalding

(57) ABSTRACT

A herbal composition enriched with Plant coagulate for the management of Gynecological disorders is envisioned. Also disclosed is a process which involves selective solvent extraction of crude herbs in contrast to conventional aqueous extraction to improve the efficacy. The extract prepared by this method, enriched with Plant coagulate is useful in the management of Gynecological disorders and to prevent/treat anaemia due to excessive bleeding associated with menstrual disorders.

The composition comprises *Saraca indica, Emblica officinalis, Terminalia chebula, Terminalia belerica, Zingiber officinale, Cyperus rotundus, Pterocarpus santalinus, Berberis aristata, Cuminum cyminum, Adhatoda vasica, Nelumbo nucifera, Piper longum, Symplocos racemosa, Woodfordia fruticosa, Mangifera indica, Spinacia oleracea, Amaranthus, Trifolium alaxandrum* and *Vigna sinensis*.

4 Claims, No Drawings

HERBAL COMPOSITION AND METHOD OF MANUFACTURING SUCH COMPOSITION FOR THE MANAGEMENT OF GYNECOLOGICAL DISORDERS

PRIORITY APPLICATION

The present application claims priority under the Paris Convention to Indian patent application entitled, "A Herbal Composition and Process for the Manufacture of such Composition for the Management of Gynecological Disorders," filed on Mar. 28, 2000 and assigned Indian Application Ser. No. 344/Del/2000.

FIELD OF INVENTION

The present invention is a herbal composition enriched with plant coagulate for the management of gynecological disorders and a process for the manufacture of such composition. In one embodiment, the herbal composition includes selected herbs in predetermined ratio ranges in combination with plant coagulate. The method of manufacture involves selective solvent extraction of crude herbs, in contrast to conventional aqueous extraction, to improve efficacy. The extract prepared by this method, enriched with plant coagulate, is useful in the management of Gynecological disorders and to prevent/treat anaemia due to excessive bleeding associated with menstrual disorders.

BACKGROUND OF INVENTION

Gynecology pertains to diseases of the female, but the term is generally used for diseases related to the female genital organs. Menstrual disorders such as dysfunctional uterine bleeding, dysmenorrhoea, irregular periods and pre-menstrual syndrome are common clinical problems in Gynecology.

Dysfunctional uterine bleeding (DUB) is defined as abnormal bleeding from the uterus in the absence of organic disease of the genital tract. Bleeding that occurs at intervals less than 21 days or more than 36 days, lasts longer than 7 days, or involves blood loss greater than 80 ml is considered abnormal. Dysfunctional uterine bleeding is characterized by menorrhagia (excessively profuse or prolonged uterine bleeding occurring at regular intervals), metrorrhagia (irregular, acyclic uterine bleeding occurring at frequent intervals), menometrorrhagia (excessive uterine bleeding occurring at irregular intervals), and polymenorrhea (bleeding occurring at regular intervals of less than 21 days). Potential causes of abnormal bleeding are numerous and include, but are not limited to, menopause, pregnancy, endometrial cancer, or fibromyomata, and thus the diagnosis of DUB must be made after careful investigation to exclude these other causes (Galle et al., Postarad Med, 93(2), 73–76 (1993)). Dysfunctional uterine bleeding is divided into anovulatory and ovulatory types. In most cases DUB is associated with anovulation (Bayer et al., JAMA, 269(14), 1823–1828 (1993)). Abnormal bleeding occurs in anovulatory cycles because of oestrogen withdrawal or oestrogen breakthrough bleeding. Oestrogen breakthrough bleeding occurs when there is continuous oestrogen stimulation of the endometrium not interrupted by cyclical progesterone secretion and withdrawal.

There are two approaches for the management of Gynecological problems—conservative and surgical. Conservative approach includes hormonal treatment with estrogenic or progestational agents (Bayer et al., JAMA, 269(14), 1823–1828 (1993)), nonsteroidal anti-inflammatory drugs and/or treatment with Ayurvedic preparations.

The constraints with the hormonal treatment and NSAID are tabulated (U.S. Pat. No. 5,552,416, Sep. 3, 1996; Shaw's textbook of Gynecology, 319, 1992)

| THERAPY | OBJECTIVE(S) | LIMITATION(S) |
|---|---|---|
| GnRH agonists | Blocks oestrogen secretion at pitutary axis level | By injection Accelerates osteoporosis Limited to preoperative use Side effects |
| Oral Progestagens | Corrects oestrogen and Progestagen ratio | Limited effectiveness Side effects |
| Nonsteroidal Anti-inflammatory Agents | Local endometrial actions | Limited effectiveness Non-specific agent Side effects |
| Oestrogen | To raise blood oestrogen level | Risk of developing carcinoma of breast and endometrium |

Because of the side effects of the hormones and NSAIDS, physicians are looking for alternative options for treatment with minimum side effects.

(1) Ayurvedic literature suggests the use of herbs such as *Saraca indica* Linn. (Ashoka) (Bhavaprakasa Nighantu, ninth edition, 500–501 (1993)), *Symplocos racemosa* Roxb.(Lodhra) (Bhavaprakasa Nighantu, ninth edition, 128–130 (1993)), *Woodfordia fruticosa* kurtz (Dhatki pushpa) (Bhavaprakasa Nighantu, ninth edition, 109–110 (1993)) etc. in the treatment of gynecological disorders.

(2) *Saraca indica* Linn. was studied for its uterine activity to understand its phenomenal use in gynecological conditions (Satyavati et al., Indian J Med Res, 58, 7 July, 1970).

(3) The following citations of different herbs exemplify known roles of herbs in the management of gynecological conditions.

(i) In Pradara (meno-metrorrhagia) one should take cold milk boiled with the decoction of ashoka bark. (Vrndamadhava 63.5)(Classical uses of Medicinal Plants by P. V. Sharma, 27, 1996).

(ii) *Symplocos racemosa* Roxb. in combination with sugar is recommended in the treatment of menorrhagia and other uterine disorders (The Wealth of India, Vol. X, 90, 1976).

(iii) Lodhra is useful in women's diseases (Classical uses of Medicinal Plants by P. V. Sharma, 333, 1996).

(a) In the eighth month, by taking Lodhra, Pippali and honey mixed together with milk, fetal movement becomes normal (Harita-samhita.3.50.5).

(b) Lodhra and Alabu leaves in equal parts should be pounded and applied as paste in the vagina in order to treat gynecological conditions. (Bhavaprakasa.ci.70.12).

(c) Lodhrasava is a popular herbal formulation for the treatment of women's diseases.

(iv) *Woodfordia fruticosa* kurtz. is used in bowel complaints and haemorrhages and is also administered in menorrhagia and seminal weakness (The Wealth of India, Vol. X, 586–587, 1976).

(v) Dhataki pushpa is used in Leucorrhoea and for conception (Classical uses of Medicinal Plants by P. V. Sharma, 204, 1996).

(a) Powder of Dhataki or Amlaki in an amoutn of 10 gm mixed with profuse honey should be used in Leucorrhoea (Vrandamadhava 63.4).

(b) Nilotpala mixed with dhataki flowers and honey is used in the morning hours to ensure conception (Gadanigraha 6.59).

(vi) Mangifera indica (Amrasthi) is used in slackness of vagina (Classical uses of Medicinal Plants by P. V. Sharma, 40, 1996).

(a) Paste is made from mango seed (Kernel), honey and camphor and applied to vagina in order to make the vagina contracted and firm. (Sarangadhara-samhita.3.11.11)

(4) Ashokarishta, a classical ayurvedic fermented product has been used to treat menstrual disorders. (Bhaishajya Ratnavali, 704, 1988).

Based on the long history of using herbs as cited above, many Ayurvedic classical and proprietary formulations contain these herbs for the treatment of gynecological problems.

There are limitations, however, to using these formulations and, therefore, there exists room to improve upon them. Below is a description of limitations present in the prior art.

(1) First, it is conventional practice to perform an aqueous extraction of crude herbs for the manufacture of Ayurvedic preparations. This, however, often results in the incomplete extraction of actives present in the plants, due to their poor solubility in water. For instance, commonly occurring plant flavonoids have estrogenic activity (Miksicek R J, Mol Pharmacol 1993, Jul.;44(1): 37–43). Even the herbs containing flavonoids are traditionally extracted with water in the manufacture of many Ayurvedic preparations. This results in lesser flavonoid content in the extract and hence is expected to show less activity.

(2) Second, the patients suffering from menstrual disorders are likely to develop anemia due to excessive bleeding. Commonly, there is a need to treat both the problems simultaneously. Unfortunately, most of the Ayurvedic preparations are designed to tackle menstrual problems ignoring the prophylactic treatment for anemia.

Plant coagulate mainly finds its application as a food supplement. The nutritional profile of plant coagulate includes protein, fat, carbohydrates, vitamins such as carotene, niacin, etc. and minerals such as calcium, phosphorous, magnesium, potassium, zinc, copper and iron.

Several publications claim the successful use of Plant coagulate in the management of malnutrition, especially in children (Shah F H et al., Qual Plant Foods Hum Nutr., 30, 245;1981; Mathur. B et al., Recent Advances in Nutriology, Volume I, 54A.).

Mathur. B et al., The Ind Nutr Diete., 26, 267; 1989, has shown the usefulness of Plant coagulate in improving hemoglobin levels in children.

(3) Third, the dose of classical liquid formulations is high and palatability is less due to an astringent taste and insitu alcohol.

SUMMARY OF THE INVENTION

The present invention discloses a novel herbal composition and a process to make an herbal extract to enhance the efficacy in treating gynecological disorders, in particular menstrual disorders. The process involves combining aqueous and organic solvent extracts of selective plants contained in the composition to perform better than conventional aqueous extract.

In one embodiment of the invention, twelve herbs are extracted with water and three herbs, which are rich in flavonoids, are extracted with 75% alcohol to get maximum flavonoid content and the extracts are then combined. The combined extract is compared with the conventional aqueous extract for their Uterotonic activity.

The combined extract obtained by this process is enriched with plant coagulate prepared by a heat coagulation method to make an herbal composition for the simultaneous treatment of gynecological conditions and resultant anemia due to excessive bleeding.

An effective amount of the herbal extract enriched with plant coagulate and conventional extract are formulated into a suitable dosage form and the improved efficacy of the herbal extract prepared by this novel process is proven by a clinical study.

DETAILED DESCRIPTION OF THE INVENTION

The present invention includes the preparation of herbal extracts by selective solvent extraction of crude herbs to improve the efficacy of the extract. The herbal extract prepared by this method is enriched with plant coagulate to make an herbal composition for the treatment of gynecological disorders.

In one embodiment, the activity of herbal extracts in the treatment of gynecological disorders is observed when the following active ingredients, both individually and in varying combinations, optionally present in the following ranges, or in other ranges that achieve the desired result.

| S.NO. | Common Name | Botanical Name | Range |
|---|---|---|---|
| 1. | Ashoka | *Saraka indica* | 1100–2100 mg |
| 2. | Lodhra | *Symplocos racemosa* | 30–400 mg |
| 3. | Dhataki | *Woodfordia fruticosa* | 40–300 mg |
| 4. | Mustaka | *Cyperus rotundus* | 5–30 mg |
| 5. | Sunthi | *Zingiber officinale* | 5–30 mg |
| 6. | Darvi | *Berberis aristata* | 5–30 mg |
| 7. | Utpala | *Nelumbo nucifera* | 5–30 mg |
| 8. | Haritaki | *Terminalia chebula* | 5–30 mg |
| 9. | Bibhitaki | *Terminalia belerica* | 5–30 mg |
| 10. | Amalaki | *Emblica officinalis* | 5–30 mg |
| 11. | Amarasthi | *Mangifera indica* | 5–30 mg |
| 12. | Jiraka | *Cuminum cyminum* | 5–30 mg |
| 13. | Vasaka | *Adhatoda vasica* | 5–30 mg |
| 14. | Chandana | *Pterocarpus santalinus* | 5–30 mg |
| 15. | Pippali | *Piper longum* | 5–30 mg |

Below is one example of the steps that may be followed to manufacture the herbal compositions of the present invention. One of ordinary skill in the art would understand that certain substitutions may be made for any traditional laboratory techniques described below.

Step I: Some of the herbs in the composition are preferably *Saraca indica, Emblica officinalis, Terminalia chebula, Terminalia belerica, Zingiber officinale, Cyperus rotundus, Pterocarous santalimus, Beriberis aristata, Cuminum cyminum, Adhatoda vasika, Nelumba nucifera* and *Piper longum*. They are coarsely powdered in a suitable cutting mill. The coarse powder is extracted with a high polar solvent preferably with sufficient water (approx. 4–10 times the quantity of powder) using suitable equipment, preferably in a open boiling pan. Once the extraction is over, the decoction is filtered through suitable filtering medium and collected in a storage tank. The herbs are again extracted with water (approx. 3–8 times) for a second time and the filtrate is collected into the storage tank. The total filtrate is concentrated to dry powder using suitable equipment like concentration pan, falling film evaporator, at atmospheric pressure or under vacuum, and/or tray drier, or by spray drying process. The extract may have a moisture content of 3–8%w/w.

Step II: Some of the herbs in the composition, preferably *Symplocos racemosa, Woodfordia fruticosa* and *Mangifera indica,* are coarsely powdered using a cutting mill. In order to effect the extraction procedure, the coarse powder is extracted in a blended solvent that includes water and an organic solvent, preferably alcohol in a defined ratio varying between 1:9 and 9:1 in a suitable apparatus. The extract obtained is concentrated in suitable equipment at atmospheric pressure or under vacuum.

Step III: The dry extracts obtained in step I & step II are mixed well. The combined extract was studied for the Uterotonic activity in comparison to conventional aqueous extract.

Step IV: Plant coagulate claimed to be useful in the treatment of iron deficiency conditions is added to the herbal extract prepared by the novel method to manage anemia associated with menstrual disorders. Plant coagulate may be prepared from any plant source and/or combined plant source. In this study, plant coagulate is prepared from any single plant or combination of two or more plants comprising mainly green leaf matter, preferably among spinach (*Spinacia oleracea*), Amaranth (*Amaranthus* spp.), Berseem (*Trifolium alaxandrum*) and Cowpea (*Vigna sinensiss*) by a suitable method, preferably heat coagulation.

The herbal composition comprising the herbal extract prepared by the novel process and Plant coagulate is formulated into a suitable dosage form. The increased efficacy of these formulations against conventional aqueous extract formulation, in the treatment of gynecological disorders and the resultant anemia due to excessive bleeding has been confirmed by a clinical study.

In one aspect according to the present invention, the active composition according to the present invention is formulated preferably in admixture with a pharmaceutically acceptable carrier. In general, it is preferable to administer the pharmaceutical composition in orally administrable form, but formulations may be administered via parenteral, intravenous, intramuscular, transdermal, buccal, subcutaneous, suppository or other route. Intravenous and intramuscular formulations are preferably administered in sterile saline. One of ordinary skill in the art may modify the formulation within the teachings of the specification to provide numerous formulations for a particular route of administration without rendering the compositions of the present invention unstable or compromising its therapeutic activity. In particular, a modification of a desired composition to render it more soluble in water or other vehicle, for example, may be easily accomplished by routine modification (salt formulation, esterification, etc.).

The amount of active composition included within therapeutically active formulations, according to the present invention, is an effective amount for treating gynecological conditions. For purposes of the present invention, a prophylactically or preventively effective amount of the compositions, according to the present invention, falls within the same concentration range for therapeutically effective amount and is usually the same as a therapeutically effective amount.

Administration of the active composition may range from continuous (intravenous drip) to several oral administrations per day (for example, Q.I.D., B.I.D., etc.) and may include oral, topical, parenteral, intramuscular, intravenous, subcutaneous, transdermal (which may include a penetration enhancement agent), buccal and suppository administration, among other routes of administration. Enteric-coated oral tablets may also be used to enhance bioavailability and stability of the composition from an oral route of administration. The most effective dosage form will depend upon the pharmacokinetics of the particular agent chosen, as well as the severity of the condition in the patient. Oral dosage forms are particularly preferred, because of ease of administration and prospective favorable patient compliance.

To prepare the pharmaceutical compositions according to the present invention, a therapeutically effective amount of the herein described composition according to the present invention is preferably mixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavoring agents, preservatives, coloring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated for sustained release by standard techniques. The use of these dosage forms may significantly impact the bioavailability of the composition in the patient.

For parenteral formulations, the carrier will usually comprise sterile water or aqueous sodium chloride solution, though other ingredients, including those which aid dispersion, also may be included. Where sterile water is to be used and maintained as sterile, the compositions and carriers must also be sterilized. Injectable suspensions may also be prepared, in which case appropriate liquid carriers, suspending agents and the like may be employed.

The invention will now be described with reference to the accompanying examples which should not be construed to limit the scope of the invention:

EXAMPLES

Example 1

A blend of *Symplocos racemosa, Woodfordia fruticosa,* and *Mangifera indica* was coarsely powdered and extractions were carried out as per the following procedures.

(a) The coarse powder was extracted with water in a steam jacketed boiling pan for 3 hours and the decoction was filtered through 100 mesh nylon cloth and collected the filtrate. The herbs were again extracted with water for another 3 hours and the filtrate was collected as earlier. The total filtrate was concentrated in steam jacketed boiling pan until viscous mass was formed. This semisolid mass was dried in hot air oven at 70–75° C. until the moisture content was brought down to below 5% w/w. The dried extract was analyzed for crude flavonoid content by an established method.

(b) The coarse powder of the above herbs was extracted with 75% alcohol in a Soxhlet apparatus for about 6 hours. The extract obtained was concentrated in a Buchi Rotavapour and finally dried in oven. The dried extract was analyzed for flavonoid content.

| Flavonoid content | |
| --- | --- |
| Aqueous extract | 1.89% w/w |
| Hydro alcoholic extract | 7.34% w/w |

Example 2

*Saraca indica, Emblica officinalis, Terminalia chebula, Terminalia belerica, Zingiber officinale, Cyperus rotundus, Pterocarpous santalimus, Beriberis aristata, Cuminum cyminum, Adhatoda vasika, Nelumba nucifera* and *Piper longum* were mixed and coarsely powdered in Retsch cutting mill using 10 mesh sieve and extracted with water as per the procedure mentioned in example 1(a).

Preparation of Samples for Studies+

Sample A: The resultant extract was mixed with the aqueous extract of the example 1(a).

Sample B: The resultant extract was mixed with the hydro alcoholic extract of the example 1(b)

The above two samples were assayed for their effect on Uterotonic activity using Wistar female albino rats.

Materials:
1. Stilbestrol dipropionate, 5-hydroxytryptamine creatinine sulphate (5-HT), De Jalon's solution, Extracts of Sample A & Sample B
2. Wistar albino rats Methods:

The uterotonic property of the test extracts were assessed in two test areas.

1. The oxytocic activity of the Sample A and Sample B is compared with uterine stimulant 5-HT.

Female rats weighing between 150–200 g were pre-treated with stilbestrol dipropionate, 1 mg/kg intra peritoneally 24 h prior to the experiment. The rats were killed by a swift blow on the head and exsanguinated. The uterus of rat dissected and the two horns divided. One horn is suspended in the bath. The rhythmic contractions are abolished by using de jalon's solution. When the spontaneous contractions became regular, the responses to Extracts of Sample A and Sample B and other agonists were recorded using a Frontal lever, isometrically connected to a polygraph.

2. Subsequently, the oxytocic activity of the Sample A is also compared with Sample B on uteri isolated from rats pre-treated with the extracts for duration up to 3 weeks.

Rats were fed orally test extracts daily for 3 weeks before sacrifice and the uterus treated as above.

| Samples | In-vitro treatment | Effect of pre-treatment on in-vitro study | Samples + 5-HT |
| --- | --- | --- | --- |
| 5-HT | Uterine contraction | Increased contraction | |
| Sample A | No Uterine contraction | Contraction | Potentiation effect |
| Sample B | No Uterine contraction | Increased contraction | Potentiation effect |

The results of the above experiments are summarized hereunder.
1. The control drug 5-HT induced a dose related increase in the height of contraction of rat isolated uterus.
2. There was no response with Sample A or Sample B on the uterus isolated from stillbestrol treated rats.
3. Pre-treatment with test samples orally for 3 weeks produced significant contractile effect as compared to the control drug 5-HT.
4. Sample B was found to be most active as it has shown the maximum height of contraction at the similar dose level.

Both the test samples used in the study failed to invoke uterotonic activity per se when used in stilbestrol primed rats. However, a pre-treatment with the test samples was found to invoke uterotonic activity; of those, sample B was found to exert a stronger effect superceding sample A.

Example 3

Preparation of Plant Coagulate:

Spinach (*Spinacia oleracea*) and Berseem (*Trifolium alaxandranum*) leaves were washed in water and then pulped separately in a chopper mill and the resultant mass was expressed to get the juice. The collected juice of Spinach and Berseem was mixed in the ratio of 1:3 respectively. The juice was heated in a boiling pan at 80–85° C. After completion of the coagulation process, coagulate was collected by filtration. Finally dried in an oven to get the combined plant coagulate.

Example 4

The herbal extract of Example 2(b) enriched with combined plant coagulate obtained in Example 3 and herbal extract of Example 2(a) were formulated into hard gelatine capsule dosage form and their efficacy had been compared by a clinical study.

| | Formulation I | |
| --- | --- | --- |
| Sl.No. | Ingredients | % w/w |
| 1. | Herbal extract of 2(b) | 35–55 |
| 2. | Combined Plant coagulate | 45–65 |
| 3. | Excipients | q.s. |

Ingredients 1, 2 & 3 were sifted through #30 sieve and mixed properly in Kenwood mixer for 15 minutes. Then the powder blend was filled in '0' size capsules using capsule filling machine.

| | Formulation II | |
| --- | --- | --- |
| Sl.No. | Ingredients | % w/w |
| 1. | Herbal extract of 2(a) | 35–55 |
| 2. | Excipients | q.s. |

The powder blend was filled in '0' size capsules.

Ten patients suffering from dysfunctional uterine bleeding and associated anemia in the same age group were enrolled. The patients were separated in to two groups consisting of 3 menorrhagia and 2 polymenorrhea patients. Group I received Formulation I and the other group received formulation II for 3 months at the dose of one capsule twice daily. Both the formulations showed activity against dysfunctional uterine bleeding, but Group I showed better activity than Group II. The patients who received Formulation I showed an increase in hemoglobin content from 8.24±0.5g/dl to 12.21±0.38 g/dl where as the patients who received formulation II showed no increase in hemoglobin content.

| Patient No. | Formulation | Diagnosis | Blood loss grading B | A | No. of pads B | A | Dry weight of pads Before g | After g |
|---|---|---|---|---|---|---|---|---|
| 1 | I | Menorrhagia | 5 | 0 | 31 | 17 | 1550 | 650 |
| 2 | I | Menorrhagia | 4 | 0 | 32 | 15 | 1600 | 750 |
| 3 | I | Menorrhagia | 3 | 0 | 31 | 14 | 1550 | 600 |
| 4 | I | Polymenorrhoea | 3 | 0 | 22 | 13 | 1200 | 750 |
| 5 | I | Polymenorrhoea | 4 | 0 | 24 | 13 | 1550 | 550 |
|   |   |   |   |   | 28 ± 4.15 | 14.4 ± 1.5 | 1490 ± 146.29 | 660 ± 80 |
| 6 | II | Menorrhagia | 4 | 0 | 36 | 18 | 1300 | 800 |
| 7 | II | Menorrhagia | 4 | 0 | 26 | 15 | 1750 | 850 |
| 8 | II | Menorrhagia | 3 | 0 | 23 | 15 | 1150 | 750 |
| 9 | II | Polymenorrhoea | 2 | 0 | 31 | 17 | 1550 | 700 |
| 10 | II | Polymenorrhoea | 2 | 0 | 25 | 14 | 1500 | 750 |
|   |   |   |   |   | 28.2 ± 4.7 | 15.8 ± 1 47 | 1450 ± 207.36 | 770 ± 50.1 |

B-Before treatment
A-After treatment

| Patient No. | Group | Diagnosis | Hemoglobin content g/dl B | A |
|---|---|---|---|---|
| 1 | I | Menorrhagia | 7.5 | 11.5 |
| 2 | I | Menorrhagia | 8.2 | 12.0 |
| 3 | I | Menorrhagia | 8.5 | 12.6 |
| 4 | I | Polymenorrhoea | 9.0 | 12.5 |
| 5 | I | Polymenorrhoea | 8.0 | 12.2 |
|   |   |   | 8.24 ± 0.5 | 12.16 ± 0.39 |
| 6 | II | Menorrhagia | 7.5 | 8.7 |
| 7 | II | Menorrhagia | 8.5 | 9.0 |
| 8 | II | Menorrhagia | 8.5 | 9.0 |
| 9 | II | Polymenorrhoea | 9.0 | 9.0 |
| 10 | II | Polymenorrhoea | 9.0 | 9.0 |
|   |   |   | 8.5 ± 0.55 | 8.94 ± 0.12 |

Duration of bleeding was also measured.

| Patient No. | Group | Diagnosis | Duration(no.of days) B | A |
|---|---|---|---|---|
| 1 | I | Menorrhagia | 12 | 4 |
| 2 | I | Menorrhagia | 6 | 3 |
| 3 | I | Menorrhagia | 7 | 4 |
|   |   |   | 8.33 ± 2.62 | 3.66 ± 0.47 |
| 6 | II | Menorrhagia | 6 | 4 |
| 7 | II | Menorrhagia | 7 | 4 |
| 8 | II | Menorrhagia | 7 | 4 |
|   |   |   | 6.66 ± 0.47 | 4 |

Since many apparently different embodiments of the present invention could be made without departing from the spirit and scope thereof, it is intended that the description of the invention herein be interpreted as being illustrative only and not limiting in any manner whatsoever.

We claim:

1. A process for the manufacture of a novel herbal composition for treating gynecological and related disorders comprising:

a) making a coarse powder of the herbs *Saraca indica, Emblica officinalis, Terminalia chebula, Terminalia belerica, Zingiber officinale, Cyperus rotundus, Pterocarpus santalinus, Berberis aristata, Cuminum cyminum, Adhatoda vasika, Nelumbo nucifera,* and *Piper longum,* extracting the said coarse powder with high polar solvent to obtain a decoction, filtering the decoction and collecting the filtrate in a storage tank, concentrating the total filtrate to a dry powder;

b) separately making a coarse powder of the herbs *Symplocos racemosa, Woodfordia fruticosa* and *Mangifera indica,* extracting the coarse powder in a blended solvent comprising water and an organic solvent to obtain an extract, concentrating the said extract;

c) extracting juice from the leaves of one or more of the herbs selected from the group consisting of Spinach (*Spinacia oleracea*), Amaranth (*Amaranthus* spp.), Berseem (*Trifolium alaxandrum*) Cowpea(*Vigna sinensis*), and any combination thereof, and separating protein by a suitable method, followed by filtration and drying of a coagulate, to obtain the plant coagulate; and d) mixing the extracts obtained in steps a) and b) and the Plant coagulate obtained in step c) to obtain the Herbal composition.

2. The process of claim 1 wherein the solvent employed for the extraction of the coarse powder of the herbs in step a) is selected from the group consisting essentially of water and alcohol.

3. The process of claim 1 wherein in step b) the organic solvent is alcohol and water in a defined ratio ranging from 1:9 or 9:1.

4. The process of claim 1 wherein in step c) the proteins are separated by heating the juice to between 40–100° C.

* * * * *